United States Patent [19]

Chang et al.

[11] Patent Number: 5,908,626
[45] Date of Patent: *Jun. 1, 1999

[54] HYBRID WITH INTERFERON-β AND AN IMMUNOGLOBULIN FC JOINED BY A PEPTIDE LINKER

[75] Inventors: Tse Wen Chang, Hsinchu, Taiwan; Liming Yu, San Diego, Calif.

[73] Assignee: Tanox, Inc., Houston, Tex.

[*] Notice: This patent is subject to a terminal disclaimer.

[21] Appl. No.: 08/994,719

[22] Filed: Dec. 19, 1997

Related U.S. Application Data

[63] Continuation-in-part of application No. 08/719,331, Sep. 25, 1996, Pat. No. 5,723,125, which is a continuation-in-part of application No. 08/579,211, Dec. 28, 1995, abandoned.

[51] Int. Cl.$^6$ ........................ A61K 39/395; A61K 39/00; C07K 1/00; C07K 16/00
[52] U.S. Cl. ................................... 424/134.1; 424/185.1; 424/192.1; 435/69.7; 530/387.3; 530/351
[58] Field of Search ................................ 530/387.3, 351; 424/134.1, 185.1, 192.1; 435/69.7; 536/23.4

[56] References Cited

U.S. PATENT DOCUMENTS

| | | |
|---|---|---|
| 4,289,689 | 9/1981 | Friesen et al. . |
| 4,973,478 | 11/1990 | Gauldi et al. . |
| 5,004,605 | 4/1991 | Hershenson et al. . |
| 5,015,730 | 5/1991 | Friesen et al. . |
| 5,349,053 | 9/1994 | Landolfi . |
| 5,428,130 | 6/1995 | Capon et al. . |
| 5,460,811 | 10/1995 | Goeddel et al. . |
| 5,468,607 | 11/1995 | Revel et al. . |
| 5,468,608 | 11/1995 | Revel et al. . |
| 5,468,609 | 11/1995 | Revel et al. . |

FOREIGN PATENT DOCUMENTS

| | | |
|---|---|---|
| 0064681 | 11/1982 | European Pat. Off. . |
| 0083069 | 6/1983 | European Pat. Off. . |
| 0083069 | 7/1983 | European Pat. Off. . |
| 0173494A2 | 5/1986 | European Pat. Off. . |
| 0207402A2 | 7/1987 | European Pat. Off. . |
| 0125256B1 | 5/1991 | European Pat. Off. . |
| 0467416 | 1/1992 | European Pat. Off. . |
| 0288809B1 | 8/1992 | European Pat. Off. . |
| 0322094B1 | 12/1992 | European Pat. Off. . |
| 0271227B1 | 6/1993 | European Pat. Off. . |
| 0325262B1 | 3/1994 | European Pat. Off. . |
| 0308936B1 | 7/1994 | European Pat. Off. . |
| 0294703B1 | 5/1995 | European Pat. Off. . |
| 0308381B1 | 3/1996 | European Pat. Off. . |
| 0325224B1 | 7/1996 | European Pat. Off. . |
| 0414178B1 | 12/1996 | European Pat. Off. . |
| 0391088B1 | 1/1997 | European Pat. Off. . |
| 0386906B1 | 4/1997 | European Pat. Off. . |
| 0314317B1 | 8/1998 | European Pat. Off. . |
| WO89/04872 | 6/1989 | WIPO . |
| WO90/02338 | 3/1990 | WIPO . |
| WO91/00360 | 1/1991 | WIPO . |
| WO91/04329 | 4/1991 | WIPO . |
| 9116353 | 10/1991 | WIPO . |

OTHER PUBLICATIONS

*Wick, Georg, et. al; "Thymic Nurse Cells . . . "; Eur. J. Immunol.; vol. 16; 1986; pp. 855–858.
*Mustelin, Tomas, et. al; "Myo–Inasitol Reverses . . . " Eur. J. Immunol.; vol. 16; 1986; pp. 859–861.
*Haak–Frendscho, M. et. al; "Inhibition of Interferon . . . " Immunology; vol. 79, 1993; pp. 594–599.
*Knapp, W. et. al; "Towards a Better Definition . . . " 1989; pp. 253–258.
*Neuberger, Michael, et. al; "Recombinant Antibodies . . . "; Nature, vol. 312, Dec. 13, 1984 p. 604–608.
*Bennett, Brian, et. al; "Extracellular Domain . . . "; Journal of Biological Chemistry; vol. 266, No. 34, Dec. 5, 1991, pp. 23060–23067.
*Gorman, Cornelia, et. al; "Transient Production . . . "; DNA & Protein Engineering Techniques; vol 2, #1, 1990, p. 3–10.
*Cosman, David; "Expression Cloning"; DNA & Protein Engineering Techniques; vol. 2, #1, 1990, p. 1–3.
*Peppel, Karsten; "A Tumor Necrosis Factor . . . "; J. Exp. Med., vol. 174, Dec. 1991; p. 148–149.
*Mark, Melanie, et. al; "Expression & Characterization . . . "; Journal of Biological Chemistry; vol. 267, No. 36, Dec. 25, 1992; pp. 26166–26171.
*Gascoigne, Nicholas; et. al; Proc. Natl. Acad. Sci USA; vol. 84, pp. 2936–2940; May 1987.
*Scallon, Bernard; et. al; "Functional Comparisons . . . "; Cytokine, vol. 7, No. 8, Nov. 1995; pp. 759–770.
*Mariuzza, Roy, et. al; "Secretion of a . . . "; Journal of Biological Chemistry, vol. 264, No. 13, May 5, 1989, pp. 7310–7316.
*Askenazi, Avi, et. al; "Protection Against . . . "; Proc. Natl. Acad. Sci, USA; vol. 88, Dec. 1991, pp. 10535–10539.
*Traunecker, Andre, et. al; "Soluble CD4 . . . "; Nature, vol. 331, Jan. 1988, pp. 84–86.
*Munro, Alan; "Uses of Chimaeric Antibodies"; Nature, vol. 312, Dec. 13, 1984; p. 597.
*Boulianne, Gabrielle; et. al; "Production of . . . "; Nature, vol. 312, Dec. 13, 1984; pp. 643–646.
*Sharon, J., et. al; "Expression of a $V_H C_k$ . . . "; Nature, vol. 309, May 24, 1984, pp. 364–367.
*Traunecker, André, et. al.; "Highly Efficient . . . "; Nature, vol. 339, May 4, 1989, pp. 68–70.
*Byrn, Randal, et. al; "Biological Properties . . . "; Nature, vol. 344, Apr. 12, 1990; pp. 667–670.
*Naldini, Luigi, et. al; "Scatter factor . . . "; The EMBO Journal, vol. 10, No. 10, 1991; pp. 2867–2878.
*deSauvage, Frederic, et. al; "Primary Structure . . . " Journal of Biological Chemistry; vol. 266, No. 27, Sep. 25, 1991 pp. 17912–17918.

(List continued on next page.)

*Primary Examiner*—Lila Feisee
*Assistant Examiner*—Susan Ungar
*Attorney, Agent, or Firm*—Eric P. Mirabel

[57] ABSTRACT

Disclosed is a hybrid recombinant protein consisting of human interferon-β, and a human immunoglobulin Fc fragment, preferably γ4 chain, joined by a peptide linker comprising the sequence Gly Gly Ser Gly Gly Ser Gly Gly Gly Gly Ser Gly Gly Gly Gly Ser (SEQ ID NO:1).

1 Claim, No Drawings

OTHER PUBLICATIONS

*Morrison, Sherie; "Transfectomas Provide . . . "; Science, vol. 229, Sep. 20, 1985; pp. 1202–1207.

*Williams, Gareth; "Production of . . . "; Gene, vol. 43, 1986, pp. 319–324.

*Morrison, Sherie, et. al; "Chimeric human . . . "; Proc. Natl. Acad. Sci. USA; vol. 81, Nov., 1984; pp. 6851–6855.

*Traunecker, Andre; et. al; "A Novel Approach . . . "; Eur. J. Immunol.; vol. 16, 1986, pp. 851–854.

*Lesslauer, Werner, et. al; "Recombinant Soluble . . . " Eur. J. Immunol., vol. 21; 1991 pp. 2883–2886.

*Becker, Michael, et. al; "Expression of a . . . "; Cell; vol. 58, Sep. 8, 1989; pp. 911–921.

Huston, JS et al, Methods in Enzymology 203:46–88.

N.F. Landolfi; Chimeric IL–2/Ig Molecule J. Immunol 146:915–919 (1991).

Peterhans, A., et al., Analytical Biochemistry 163(2)470–75.

Baron, E. and Narula, S., *Biotechnology*, 10:179–190, 1990, From cloning to commercial realization: Human alpha interferon.

Bocci, V., *Interferon*, 4:47–72, 1985, Distribution, catabolism and pharmacokinetics of interferons.

Bohoslawec, O. et al., *J. Interferon Res.*, 6:207–213, 1986, Pharmacokinetics and tissue distribution of recombinant human alpha A, D, A/D(Bgl), and I interferons and mouse alpha–interferon in Mice.

Bonetti, A. and Kim, S. *Cancer Chemother Pharmacol.* 33:258–261, 1993, Pharmacokinetics of an extended–release human interferon alpha–2b formulation.

Brown, K.D. *Genetic Engineering News*, 15:1–35, 1995, Novel emerging therapeutics target the hepatitis C virus.

Brunt, J.V., *Biotechnology*, 7:549, 1989, Interferon trials proliferate.

Cantell, K. et al., *Methods in Enzymology*, 78A:29–38, Adacemic Press, 1981.

Coligan, J.E. et al., *Current protocols in immunology*, pp. 6.9.1–6.9.8, Current Protocols, 1991, Measurement of antiviral activity induced by interferon $\alpha$, $\beta$, and $\gamma$.

Daugherty, B.L. et al., *Nucleic Acids Res.* 19:2471–6, 1991, Polymerase chain reaction facilitates the cloning, CDR–grafting, and rapid expression of murine monoclonal antibody directed against the CD18 component of leukocyte integrins.

Dianzani, F. *J. Interferon Res.* (*Special Issue*) 109:118, 1992, Interferon treatments: how to use an endogenous system as a therapeutic agent.

Evinger, M. and Pestka, S., *Methods in Enzymology*, 79:362–8, Assay of growth inhibition in lymphoblastoid cell cultures.

Goeddel, D.V. et al., *Nature*, 290:20–26, 1981, The structure of eight distinct cloned human leukocyte interferon dDNAs.

Gutterman, J., *Proc. Natl. Aca. Sci.* 91:1198–1205;1994, Cytokine therapeutics: lessons from interferon $\alpha$.

Johns, T.G. et al., *Cancer Res.*, 50:4718–23, 1990, Pharmacokinetics, tissue distribution, and cell localization of [$^{35}$S] methionine–labeled recombinant human and murine $\alpha$ interferons in mice.

Kabat, E.A. et al., *Sequences of proteins of immunological interest*, pp. 1582–1598, NIH, 1991.

Kurschner, C. et al., *J. Immunol.* 149:4096–4100, 1992, IFN–$\gamma$ receptor–Ig fusion proteins.

Mordenti J. et al., *Nature*, 337:525–31, 1989, Designing CD4 immunoadhesins for AIDS therapy.

Quesada, J.R. et al., *J. Clin. Oncol.* 4:234–243, 1986, Clinical toxicity of interferons in cancer patients: a review.

Roche Labs., Referon A, Schering, Intron A, *Physicians' Desk Reference*, 47 edition, 1993, pp. 2006–2008, 2194–2201.

Roitt. I., *Essential Immunology*, 7th edition, 1991, Blackwell Scientific Publications, pp. 45–51, Immunoglubulin classies and subclasses.

Saiki, R.K. et al., *Science*, 239:487, 1988, Primer–directed enzymatic amplification of DNA with a thermostable DNA polymerase.

Sambrook, J. et al., *Molecular cloning*, 1989, Cold Spring Harbor Laboratory Press, pp. 16.28–16.29.

Schein, C.H. and Noteborn, H.M., *Bio/technology*, 6:291–294, 1988, Formation of soluble recombinant proteins in *Escherichia coli* is favored by lower growth temperature.

Scorer, C.A. et al.,*Gene*, 136:111–9, 1993, The intracellular production and secretion of HIV–1 envelope protein in the methylotrophic yeast *Pichia pastoris*.

Strander, H. *Adv. Cancer Res.* 46:1–265, 1986, Interferon treatment of human neoplasia.

Tabata, Y. et al., *Cancer Res.* 51:5532–8, 1991, Effects of recombinant alpha–interferon–gelatin conjugate on in vivo murine tumor cell growth.

von Gabain, A., et al., *Eur. J. Biochem.* 190:257–61, 1990, Three human interferon–$\alpha$2 subvariants disclose structural and functional differences.

Weissmann, C. and Weber, H. *Prog. Nuc. Acid Res. Mol. Biol.* 33:251–300, 1986, The interferon genes.

Wilkinson, D.L. and Harrison, R.G., *Bio/technology*, 9:443–448, 1991, Predicting the solubility of recombinant proteins in *Escherichia coli*.

Zoon, K.C. *Interferon*, 9:1–12, 1987, Human interferons: structure and function.

ID NO:1)). This peptide itself is immunologically inactive. The
HYBRID WITH INTERFERON-β AND AN IMMUNOGLOBULIN FC JOINED BY A PEPTIDE LINKER This application is a continuation-in-part of U.S. application Ser. No. 08/719,331, filed Sep. 25, 1996, now U.S. Pat. No. 5,723,125 which is a continuation-in-part of U.S. application Ser. No. 08/579,211, filed Dec. 28, 1995, now abandoned.

BACKGROUND OF THE INVENTION

Interferons, including interferon-α ("IFNα") and interferon-β ("IFNβ"), were among the first of the cytokines to be produced by recombinant DNA technology. IFNα has been shown to have therapeutic value in conditions such as inflammatory, viral, and malignant diseases. IFNβ has been approved for use in treatment of multiple sclerosis.

Most cytokines, including IFNβ, have relatively short circulation half-lives since they are produced in vivo to act locally and transiently. To use IFNβ as an effective systemic therapeutic, one needs relatively large doses and frequent administrations. Such frequent parenteral administrations are inconvenient and painful. Further, toxic side effects are associated with IFNβ administration which are so severe that some multiple sclerosis patients cannot tolerate the treatment. These side effects are probably assciated with administration of a high dosage.

To overcome these disadvantages, one can modify the molecule to increase its circulation half-life or change the drug=s formulation to extend its release time. The dosage and administration frequency can then be reduced while increasing the efficacy. With respect to interferon-α, which suffers from the same disadvantages, efforts have been made to create a recombinant IFNα-gelatin conjugate with an extended retention time (Tabata, Y. et al., *Cancer Res.* 51:5532–8, 1991). A lipid-based encapsulated IFNα formulation has also been tested in animals and achieved an extended release of the protein in the peritoneum (Bonetti, A. and Kim, S. *Cancer Chemother Pharmacol.* 33:258–261, 1993).

Immunoglobulins of IgG and IgM class are among the most abundant proteins in the human blood. They circulate with half-lives ranging from several days to 21 days. IgG has been found to increase the half-lives of several ligand binding proteins (receptors) when used to form recombinant hybrids, including the soluble CD4 molecule, LHR, and the IFN-γ receptor (Mordenti J. et al., *Nature*, 337:525–31, 1989, Capon, D. J. and Lasky, L. A., U.S. Pat. No. 5,116, 964; Kurschner, C. et al., *J. Immunol.* 149:4096–4100, 1992). However, such hybrids can present problems in that the peptide at the C-terminal of the active moeity and the peptide at the N-terminal of the Fc portion at the fusion point creates a new peptide sequence, which is a neoantigen, and which can be immunogenic. The invention relates to a IFNβ-Fc hybrid which is designed to overcome this problem and extend the half-life of the IFNβ.

SUMMARY OF THE INVENTION

The present invention relates to a hybrid recombinant protein which consists of two subunits. Each subunit includes a human interferon, preferably IFNβ, joined by a peptide linker which is primarily composed of a T cell inert sequence, linked to a human immunoglobulin Fc fragment, preferably the γ4 chain. The γ4 chain is preferred over the γ1 chain because the former has little or no complement activating ability.

The C-terminal end of the IFNβ is linked to the N-terminal end of the Fc fragment. An additional IFNβ (or other cytokine) can attach to the N-terminal end of any other unbound Fc chains in the Fc fragment, resulting in a homodimer for the γ4 chain. If the Fc fragment selected is another chain, such as the μ chain, then, because the Fc fragments form pentamers with ten possible binding sites, this results in a molecule with interferon, or another cytokine, linked at each of ten binding sites.

The two moieties of the hybrid are linked through a T cell immunologically inert peptide (e.g., Gly Gly Ser Gly Gly Ser Gly Gly Gly Gly Ser Gly Gly Gly Gly Ser (SEQ ID NO:1)). This peptide itself is immunologically inactive. The insertion of this peptide at the fusion point eliminates the neoantigenicity created by the joining of the two peptide moeities. The linker peptide also increases the flexibility of these moieties and allows retention of the biological activity. This relatively long linker peptide helps overcome the possible steric hindrance from the Fc portion of the hybrid, which could interfere with the activity of the hybrid.

The hybrid should have a much longer half-life than the native IFNβ, based on experiments with a similar hybrid but in which IFNα is the cytokine moiety. Due to the linker, the hybrid is also designed to reduce the possibility of generating a new immunogenic epitope (a neoantigen) at what would otherwise be the fusion point of the IFNβ and the immunoglobulin Fc segment.

Cytokines are generally small proteins with relatively short half-lives which dissipate rapidly among various tissues, including at undesired sites. It is believed that small quantities of some cytokines can cross the blood-brain barrier and enter the central nervous system, thereby causing severe neurological toxicity. The IFNβ linked to Fcγ of the present invention would be especially suitable for treating multiple sclerosis, because these products will have a long retention time in the vasculature (upon intravenous adminstration) and will not penetrate undesired sites.

BRIEF DESCRIPTION OF THE SEQUENCE LISTING

SEQ ID NO:1 is the unique peptide linker which conjugates the N-terminal end(s) of a heavy chain γ4 Fc fragment to an interferon-β moiety.

SEQ ID NO:2 is the nucleotide and amino acid sequence of interferon-β.

SEQ ID NO:3 is the nucleotide and amino acid sequence of interferon-5, the unique peptide linker, and an Fc immunoglobulin moiety.

DETAILED DESCRIPTION OF MAKING AND USING THE INVENTION

The hybrid molecule of the invention includes an interferon-β moiety linked through a unique linker to an immunoglobulin Fc moiety. Preferably, the C-terminal ends of two interferon moieties are separately attached to each of the two N-terminal ends of a heavy chain γ4 Fc fragment, resulting in a homodimer structure. A unique linker peptide, Gly Gly Ser Gly Gly Ser Gly Gly Gly Gly Ser Gly Gly Gly Gly Ser (SEQ ID NO:1), was created to link the two moieties. The complete nucleotide sequence of the preferred hybrid (including the linker and the Fc moiety) appears in SEQ ID NO: 3. The linker is located at amino acid residue numbers 188 to 203.

The advantage of the hybrid over the native cytokine is that the half-life in vivo is longer. The hybrid including interferon and the γ4 chain Fc homodimer is larger than the native interferon. Because the pores in the blood vessels of the liver are large, this larger molecule is more suitable for use in treating hepatitis, where the virus responsible primarily affects the liver.

The linker peptide is designed to increase the flexibility of the two moieties and thus maintain their biological activity. Although the interferon and the immunoglobulin are both of human origin, there is always a possibility of generating a new immunogenic epitope at the fusion point of the two molecules. Therefore, the other advantage of the linker of the invention, which consists mainly of a T cell inert sequence, is to reduce immunogenicity at the fusion point. Referring to SEQ ID NO:3, it can be seen that if the linker (residue numbers 188 to 203) was not present, a new sequence consisting of the fusion point residues would be created. This new sequence would be a neoantigen for the human body.

IFNβ is approved for use in treating multiple sclerosis. It may have other therapeutic uses as well. It is nearly as well studied and characterized as is interferon-α.

The advantages of the γ4 chain as the Fc moiety in the hybrid is that it is stable in the human circulation. The γ4 chain (unlike the γ1 chain) also avoids the wide spectrum of secondary biological properties, such as complement fixation and antibody-dependant cell-mediated cytotoxicity (ADCC), which may be undesirable properties.

The cDNA of the IFNβ can be obtained by reverse transcription and PCR, using RNA extracted from leukocytes which express IFNβ, and following the extraction with reverse transcription and expression in a standard expression system.

There are several ways to express the recombinant protein in vitro, including in E. coli, baculovirus, yeast, mammalian cells or other expression systems. The prokaryotic system, E. coli, is not able to do post-translational modification, such as glycosylation. This could be a problem in these systems, and mammalian expression could be preferred for this reason.

There are also several other advantages to this mammalian expression system. First, the recombinant protein is secreted into the culture supernatant and there is no aggregation or inclusion bodies, thereby simplifying purification. One chromatography step using a protein A column yields a purified IFNα-Fc protein. Also, the protein produced in this system has a glycosylation pattern very similar to the natural molecules since it is expressed by mammalian cells.

As mentioned above, the purification of the IFNβ-Fc recombinant protein from the culture supernatant is relatively straightforward. The protein with a purity of more than 90%, as judged by SDS-PAGE, can be easily obtained by one step of affinity chromatography with a protein A column.

There are several assay methods available for the measuring of the IFNβ bioactivity, including an antiviral assay. The hybrid of SEQ ID NO:3 is expected to have a longer half-life in vivo than native IFNβ based on results achieved using the same hybrid, but with interferonα as the cytokine. Even though its specific activity is lower, this novel hybrid is expected to be preferred to the native IFNβ for clinical use. This is because, as a result of the longer half-life, the Cxt (the area under the concentration vs. time curve) would be up to several hundred times greater than for the native IFNβ. This means that at the equivalent molar dosage of the native IFNβ and the hybrid, the latter would provide a several hundred fold increased exposure to IFNβ, resulting in vastly increased efficacy at the same dosage, and less frequent administration.

It should be understood that the terms and expressions used herein are exemplary only and not limiting, and that the scope of the invention is defined only in the claims which follow, and includes all equivalents of the subject matter of those claims.

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
       (A) LENGTH: 48 nucleic acids
       (B) TYPE: Nucleic Acid
       (C) STRANDEDNESS: double stranded
       (D) TOPOLOGY: linear (xi) SEQUENCE DESCRIPTION: SEQ ID NO:1:

GGT GGC TCA GGT GGA TCC GGT GGA GGC GGA AGC GGC                36
Gly Gly Ser Gly Gly Ser Gly Gly Gly Gly Ser Gly
 1               5                   10

GGT GGA GGA TCA                                                48
Gly Gly Gly Ser
        15

(2) INFORMATION FOR SEQ ID NO:2:

(i) SEQUENCE CHARACTERISTICS:
       (A) LENGTH: 561 nucleic acids
       (B) TYPE: nucleic acid
       (C) STRANDEDNESS: double stranded (D) TOPOLOGY: linear (xi) SEQUENCE DESCRIPTION: SEQ ID NO:2:

```
ATG ACC AAC AAG TGT CTC CTC CAA ATT GCT CTC CTG TTG TGC TTC        45
Met Thr Asn Lys Cys Leu Leu Gln Ile Ala Leu Leu Leu Cys Phe
 1               5                  10                  15

TCC ACT ACA GCT CTT TCC ATG AGC TAC AAC TTG CTT GGA TTC CTA        90
Ser Thr Thr Ala Leu Ser Met Ser Tyr Asn Leu Leu Gly Phe Leu
                20                  25                  30

CAA AGA AGC AGC AAT TTT CAG TGT CAG AAG CTC CTG TGG CAA TTG       135
Gln Arg Ser Ser Asn Phe Gln Cys Gln Lys Leu Leu Trp Gln Leu
         35                  40                  45

AAT GGG AGG CTT GAA TAC TGC CTC AAG GAC AGG ATG AAC TTT GAC       180
Leu Leu Trp Leu Glu Tyr Cys Leu Lys Asp Arg Met Asn Phe Asp
                50                  55                  60

ATC CCT GAG GAG ATT AAG CAG CTG CAG CAG TTC CAG AAG GAG GAC       225
Ile Pro Glu Glu Ile Lys Gln Leu Gln Gln Phe Gln Lys Glu Leu
                65                  70                  75

GCC GCA TTG ACC ATC TAT GAG ATG CTC CAG AAC ATC TTT GCT ATT       270
Thr Ile Asp Ala Ala Tyr Glu Met Leu Gln Asn Ile Phe Ala Ile
                80                  85                  90

TTC AGA CAA GAT TCA TCT AGC ACT GGC TGG AAT GAG ACT ATT GTT       315
Phe Arg Gln Asp Ser Ser Ser Thr Gly Trp Asn Glu Thr Ile Val
                95                 100                 105

GAG AAC CTC CTG GCT AAT GTC TAT CAT CAG ATA AAC CAT CTG AAG       360
Glu Asn Leu Leu Ala Asn Val Tyr His Gln Ile Asn His Leu Lys
               110                 115                 120

ACA GTC CTG GAA GAA AAA CTG GAG AAA GAA GAT TTC ACC AGG ATG       405
Thr Val Leu Glu Glu Lys Leu Glu Lys Glu Asp Phe Thr Arg Met
               125                 130                 140

AGC AGT GGA AAA CTC CTG CAC CTG AAA AGA TAT TAT GGG AGG ATT       450
Ser Ser Gly Lys Leu Leu His Leu Lys Arg Tyr Tyr Gly Arg Ile
               145                 150                 155

CTG CAT TAC CTG AAG GCC AAG GAG TAC AGT CAC TGT GCC TGG ACC       495
Leu His Tyr Leu Lys Ala Lys Glu Tyr Ser His Cys Ala Trp Thr
               160                 165                 170

ATA GTC AGA GTG GAA ATC CTA AGG AAC TTT TAC TTC ATT AAC AGA       540
Ile Val Arg Val Glu Ile Leu Arg Asn Phe Tyr Phe Ile Asn Arg
               175                 180                 185

CTT ACA GGT TAC CTC CGA AAC                                       561
Leu Thr Gly Tyr Leu Arg Asn
               190
```

(2) INFORMATION FOR SEQ ID NO:3:

(i) SEQUENCE CHARACTERISTICS:
        (A) LENGTH: 1299 nucleic acids
        (B) TYPE: nucleic acid
        (C) STRANDEDNESS: double stranded
        (D) TOPOLOGY: linear (xi) SEQUENCE DESCRIPTION: SEQ ID NO:3:

```
ATG ACC AAC AAG TGT CTC CTC CAA ATT GCT CTC CTG TTG TGC TTC        45
Met Thr Asn Lys Cys Leu Leu Gln Ile Ala Leu Leu Leu Cys Phe
 1               5                  10                  15

TCC ACT ACA GCT CTT TCC ATG AGC TAC AAC TTG CTT GGA TTC CTA        90
Ser Thr Thr Ala Leu Ser Met Ser Tyr Asn Leu Leu Gly Phe Leu
                20                  25                  30

CAA AGA AGC AGC AAT TTT CAG TGT CAG AAG CTC CTG TGG CAA TTG       135
Gln Arg Ser Ser Asn Phe Gln Cys Gln Lys Leu Leu Trp Gln Leu
         35                  40                  45

AAT GGG AGG CTT GAA TAC TGC CTC AAG GAC AGG ATG AAC TTT GAC       180
```

-continued

| | | | | | | | | | | | | |
|---|---|---|---|---|---|---|---|---|---|---|---|---|
| Leu | Leu | Trp | Leu | Glu | Tyr | Cys | Leu | Lys | Asp | Arg | Met | Asn | Phe | Asp |
| | | | 50 | | | | | 55 | | | | | 60 | |

ATC CCT GAG GAG ATT AAG CAG CTG CAG CAG TTC CAG AAG GAG GAC      225
Ile Pro Glu Glu Ile Lys Gln Leu Gln Gln Phe Gln Lys Glu Asp
            65                  70                  75

GCC GCA TTG ACC ATC TAT GAG ATG CTC CAG AAC ATC TTT GCT ATT      270
Thr Ile Asp Ala Ala Tyr Glu Met Leu Gln Asn Ile Phe Ala Ile
            80                  85                  90

TTC AGA CAA GAT TCA TCT AGC ACT GGC TGG AAT GAG ACT ATT GTT      315
Phe Arg Gln Asp Ser Ser Ser Thr Gly Trp Asn Glu Thr Ile Val
            95                 100                 105

GAG AAC CTC CTG GCT AAT GTC TAT CAT CAG ATA AAC CAT CTG AAG      360
Glu Asn Leu Leu Ala Asn Val Tyr His Gln Ile Asn His Leu Lys
           110                 115                 120

ACA GTC CTG GAA GAA AAA CTG GAG AAA GAA GAT TTC ACC AGG ATG      405
Thr Val Leu Glu Glu Lys Leu Glu Lys Glu Asp Phe Thr Arg Met
           125                 130                 135

AGC AGT GGA AAA CTC CTG CAC CTG AAA AGA TAT TAT GGG AGG ATT      450
Ser Ser Gly Lys Leu Leu His Leu Lys Arg Tyr Tyr Gly Arg Ile
           140                 145                 150

CTG CAT TAC CTG AAG GCC AAG GAG TAC AGT CAC TGT GCC TGG ACC      495
Leu His Tyr Leu Lys Ala Lys Glu Tyr Ser His Cys Ala Trp Thr
           155                 160                 165

ATA GTC AGA GTG GAA ATC CTA AGG AAC TTT TAC TTC ATT AAC AGA      540
Ile Val Arg Val Glu Ile Leu Arg Asn Phe Tyr Phe Ile Asn Arg
           170                 175                 180

CTT ACA GGT TAC CTC CGA AAC                                      561
Leu Thr Gly Tyr Leu Arg Asn
           185

GGT GGC TCA GGT GGA TCC GGC GGA GGC GGA AGC GGC GGT GGA GGA TCA  609
Gly Gly Ser Gly Gly Ser Gly Gly Gly Gly Ser Gly Gly Gly Gly Ser
           190                 195                 200

GAG TCC AAA TAT GGT CCC CCG TGC CCA TCA TGC CCA GCA CCT GAG GAG  654
Glu Ser Lys Tyr Gly Pro Pro Cys Pro Ser Cys Pro Ala Pro Glu Glu
           205                 210                 215

TTC CTG GGG GGA CCA TCA GTC TTC CTG TTC CCC CCA AAA              693
Phe Leu Gly Gly Pro Ser Val Phe Leu Phe Pro Pro Lys
           220                 225                 230

CCC AAG GAC ACT CTC ATG ATC TCC CGG ACC CCT GAG GTC              732
Pro Lys Asp Thr Leu Met Ile Ser Arg Thr Pro Glu Val
           235                 240

ACG TGC GTG GTG GTG GAC GTG AGC CAG GAA GAC CCC GAG              771
Thr Cys Val Val Val Asp Val Ser Gln Glu Asp Pro Glu
           245                 250                 255

GTC CAG TTC AAC TGG TAC GTG GAT GGC GTG GAG GTG CAT              810
Val Gln Phe Asn Trp Tyr Val Asp Gly Val Glu Val His
           260                 265

AAT GCC AAG ACA AAG CCG CGG GAG GAG CAG TTC AAC AGC              849
Asn Ala Lys Thr Lys Pro Arg Glu Glu Gln Phe Asn Ser
270             275                 280

ACG TAC CGT GTG GTC AGC GTC CTC ACC GTC CTG CAC CAG              888
Thr Tyr Arg Val Val Ser Val Leu Thr Val Leu His Gln
           285                 290                 295

GAC TGG CTG AAC GGC AAG GAG TAC AAG TGC AAG GTC TCC              927
Asp Trp Leu Asn Gly Lys Glu Tyr Lys Cys Lys Val Ser
           300                 305

AAC AAA GGC CTC CCG TCC TCC ATC GAG AAA ACC ATC TCC              966
Asn Lys Gly Leu Pro Ser Ser Ile Glu Lys Thr Ile Ser
           310                 315                 320

AAA GCC AAA GGG CAG CCC CGA GAG CCA CAG GTG TAC ACC             1005
Lys Ala Lys Gly Gln Pro Arg Glu Pro Gln Val Tyr Thr

| | | |
|---|---|---|
| Lys Ala Lys Gly Gln Pro Arg Glu Pro Gln Val Tyr Thr<br>             325                   330 | | |
| CTG CCC CCA TCC CAG GAG GAG ATG ACC AAG AAC CAG GTC<br>Leu Pro Pro Ser Gln Glu Glu Met Thr Lys Asn Gln Val<br>335                 340                 345 | | 1044 |
| AGC CTG ACC TGC CTG GTC AAA GGC TTC TAC CCC AGC GAC<br>Ser Leu Thr Cys Leu Val Lys Gly Phe Tyr Pro Ser Asp<br>            350                 355                 360 | | 1083 |
| ATC GCC GTG GAG TGG GAG AGC AAT GGG CAG CCG GAG AAC<br>Ile Ala Val Glu Trp Glu Ser Asn Gly Gln Pro Glu Asn<br>                 365                 370 | | 1122 |
| AAC TAC AAG ACC ACG CCT CCC GTG CTG GAC TCC GAC GGC<br>Asn Tyr Lys Thr Thr Pro Pro Val Leu Asp Ser Asp Gly<br>            375                 380                 385 | | 1161 |
| TCC TTC TTC CTC TAC AGC AGG CTA ACC GTG GAC AAG AGC<br>Ser Phe Phe Lys Tyr Ser Arg Leu Thr Val Asp Lys Ser<br>                 390                       395 | | 1200 |
| AGG TGG CAG GAG GGG AAT GTC TTC TCA TGC TCC GTG ATG<br>Arg Trp Gln Glu Gly Asn Val Phe Ser Cys Ser Val Met<br>400                 405                     410 | | 1239 |
| CAT GAG GCT CTG CAC AAC CAC TAC ACA CAG AAG AGC CTC<br>His Glu Ala Leu His Asn His Tyr Thr Gln Lys Ser Leu<br>            415                 420 | | 1278 |
| TCC CTG TCT CTG GGT AAA TAG<br>Ser Leu Ser Leu Gly Lys<br>425                 430 | | 1299 |

What is claimed is:

1. A hybrid molecule comprising an interferon-β molecule joined at its C-terminal end through a peptide linker to the N-terminal end of an immunoglobulin γ4 chain Fc fragment, the peptide linker comprising the sequence Gly Gly Ser Gly Gly Ser Gly Gly Gly Gly Ser Gly Gly Gly Gly Ser (SEQ ID NO:1).

* * * * *